United States Patent  
Badger

(10) Patent No.: US 10,245,173 B2  
(45) Date of Patent: Apr. 2, 2019

(54) METHOD AND SYSTEM FOR RELIEVING AND PREVENTING EXCESSIVE BACK AND JOINT DISCOMFORT, POOR POSTURE, AND LACK OF ENERGY

(71) Applicant: Posture Newmatic Technologies, LLC, Allen, TX (US)

(72) Inventor: David A. Badger, Allen, TX (US)

( * ) Notice: Subject to any disclaimer, the term of this patent is extended or adjusted under 35 U.S.C. 154(b) by 0 days.

(21) Appl. No.: 16/028,345

(22) Filed: Jul. 5, 2018

(65) Prior Publication Data
US 2019/0015235 A1 Jan. 17, 2019

Related U.S. Application Data

(60) Provisional application No. 62/531,164, filed on Jul. 11, 2017.

(51) Int. Cl.
*A61F 5/02* (2006.01)
*A61H 23/02* (2006.01)
*A61H 1/00* (2006.01)

(52) U.S. Cl.
CPC .............. *A61F 5/026* (2013.01); *A61F 5/024* (2013.01); *A61F 5/028* (2013.01); *A61H 1/008* (2013.01); *A61H 23/02* (2013.01); *A61H 2201/1626* (2013.01)

(58) Field of Classification Search
CPC ...... A61H 1/02; A61H 1/0274; A61H 1/0281; A61H 1/0296; A61H 1/0292; A61H 1/008; A61H 23/02; A61H 2201/1626; A61F 5/026; A61F 5/024; A61F 5/028
USPC ..................................................... 602/19, 32
See application file for complete search history.

*Primary Examiner* — Ophelia A Hawthorne
(74) *Attorney, Agent, or Firm* — Hulsey P.C.

(57) ABSTRACT

A posture alignment system improves posture by posture modification and spinal alignment. A back plate for positioning along a user's back provides a rigid structural foundation. A separation plate hingedly couples to the posture alignment system. A spinal mold mechanism includes a spinal mold positioned on the spinal mold plate for interfacing and providing posture modifying support and alignment force to the user's spine. The spinal mold includes posture alignment guide rails for guiding posture modification and spinal alignment according to a posture alignment goal. A pneumatic force generating mechanism controllably generates pneumatic force for forcibly and controllably interfacing the spinal mold mechanism and the neck aligning mechanism with the user's spine and neck, and, thereby guide posture modification and spinal alignment of the user according to the posture alignment goal.

19 Claims, 12 Drawing Sheets

METHOD AND SYSTEM FOR RELIEVING AND PREVENTING EXCESSIVE BACK AND JOINT DISCOMFORT, POOR POSTURE, AND LACK OF ENERGY

CROSS REFERENCE TO RELATED APPLICATION

This application claims the benefit of the following non-provisional application, all of which is here expressly incorporated by reference in its entirety:

62/531,164 entitled "METHOD AND SYSTEM FOR RELIEVING AND PREVENTING EXCESSIVE BACK DISCOMFORT, POOR POSTURE, AND LACK OF ENERGY," filed on Jul. 11, 2017;

FIELD OF THE DISCLOSURE

The present disclosure relates to therapeutic devices for relieving and preventing back pain and, more particularly to methods and systems for relieving and preventing excessive back discomfort, poor posture, and lack of energy.

BACKGROUND OF THE DISCLOSURE

Back and/or joint pain may be the result of a series of small but gradual misalignments in the user's posture. Posture misalignments are sometimes so gradual that pain is their first noticeable symptom. Back and joint pain may be alleviated and the misalignments may be corrected without prescriptions or surgery thanks to our patented new technology. However, the means for achieving this relief are limited.

Posture is generally not predetermined by bone structure, but is determined over time by the force applied to the skeleton each day. That is, while individuals may be genetically predisposed to develop poor posture, these tendencies may be countered.

In addition, a frequent problem with poor posture is a lack of energy from the body diverting critical energy to the muscles and joints burdened by unhealthy pressure. To compensate, individuals may resort to artificial supplements to provide energy. With corrected posture, however, a person will move efficiently, so that natural efficiencies provide the needed energy.

A sedentary daily routine that positions the user's body unnaturally may generate unhealthy force that may cause of painful, unflattering, and inefficient misalignments. The longer a person delays corrective action, the more severe will be these misalignments, and their symptoms.

One common back problem is known as kyphosis, which is a spinal deformity that may take several forms. The subject matter of the present disclosure may provide an appropriate treatment for kyphosis depending on the cause of the condition as well as severity of symptoms.

Degenerative kyphosis develops due to wear and tear on the spine over time. The underlying cause of the kyphosis typically is spinal arthritis with degeneration of the discs. Non-surgical treatments, such as pain medication, exercise and physical therapy are typically helpful treatments for pain. Surgery may be an option, but is uncommon for this diagnosis. Neuromuscular kyphosis may occur in children with certain neuromuscular disorders, such as cerebral palsy, spina bifida, or muscular dystrophy. Surgery may be an option to improve quality of life.

Nutritional kyphosis occurs due to certain vitamin deficiencies during childhood, such as a vitamin D deficiency. Postural kyphosis occurs due to poor posture and slouching. It occurs in both young and older patients, is more prominent in females than in males, and rarely causes pain. Scheuermann's kyphosis occurs in adolescents due to abnormal growth of the spine and discs. It may become clinically evident in adolescents or adults, and is more common in males.

Traumatic kyphosis may occur from misaligned healing of a spinal fracture or injury to the supporting ligaments of the spine. Iatrogenic kyphosis may develop as a complication of surgical treatment of the spine. Post-laminectomy kyphosis is the most common type of iatrogenic kyphosis, which may develop following decompressive spine surgery requiring removal of the posterior elements of the spine (the spinous processes, laminae, and intervening ligaments), typically for tumor removal in children and adolescents.

If kyphosis is suspected, it is advisable for patients to consult their primary care physician, chiropractor, or other spine specialist to obtain an accurate diagnosis through a physical exam, patient history and, as appropriate, diagnostic imaging such as X-ray or MRI scan. Through this consultation, various back health therapies may be prescribed. One such therapy may include a brace or other supportive or back alignment corrective device. To date, however, the known forms of braces or supportive/corrective devices have proved to be ineffective or wanting in many ways. Accordingly, there is the need for a system that may be used by a wide variety of patients experiencing kyphosis or back pain that is minimally invasive, easy and inexpensive to use.

A need exists for improvement in the ways that back braces or supportive/corrective devices benefit the patient. Such a device should provide progressive relief and realignment, as necessary, for the patient.

SUMMARY OF THE DISCLOSURE

The present disclosure provides a solution to end common back problems, including excessive back discomfort, poor posture, and lack of energy with uncommon solutions that avoid surgery and drugs. The subject matter of the present disclosure relieves excessive back discomfort, poor posture, and a lack of energy to complete relief in a manner that is easier to obtain than generally thought possible. The subject matter of the present disclosure provides a therapeutic device that can, in some cases, reverse and prevent these types of common back problems quickly, safely, and effectively; keeping the user off the operating table and potentially harmful drugs.

According to one aspect of the present disclosure, here appears a posture alignment system for improving the posture of a user by posture modification and spinal alignment. The novel and inventive subject matter includes a back plate for positioning the posture alignment system along a user's back and in alignment with the spine when the user is standing. The back plate provides a rigid structural foundation extending from approximately the user's head down vertically to at least to the user's hip region. A separation plate hingedly couples to the posture alignment system at a position near the user's hip region when positioning the posture alignment system along the user's back. The separation plate has a length approximately the length of the back plate may be positioned in parallel with the back plate for forming a first variable wedge space from the back plate upon being pivoted at the hinged coupling.

A spinal mold mechanism has a length approximately equivalent to that of and positioned in parallel with the separation plate. The spinal mold mechanism hingedly couples to the posture alignment system near the user's hip region when positioning the posture alignment system along the user's back. The spinal mold mechanism includes a spinal mold positioned on the spinal mold plate and has a length equal to at least approximately the length of the user's spine for interfacing and providing posture modifying support and alignment force to the user's spine. The spinal mold includes posture alignment guide rails for guiding posture modification and spinal alignment according to a posture alignment goal. A spinal mold plate for providing structural support and foundation for the spinal mold and for forming a second variable wedged space from the separation plate upon being pivoted at the hinged coupling.

A neck aligning mechanism on the posture alignment system is above the spinal mold when positioning the posture alignment system along the user's back for aligning the position of the user's neck with the user's spine. In this configuration, the posture alignment guide rails guide the posture modification and spinal alignment.

A user harnessing mechanism harnesses the posture alignment system to the user. The user harnessing system includes a head harnessing mechanism further including at least one head harness for firmly harnessing the user's head and a tether harness for firmly connecting set head harness to the back plate. A shoulder harness mechanism including at least one harness for each shoulder of the user for firmly harnessing the user's shoulders to the spinal mold mechanism. A hip harness for harnessing the user's hips to the posture alignment system.

A pneumatic force generating mechanism associates with the back plate, the separation plate, and the spinal mold mechanism for controllably generating pneumatic force at the spinal mold back plate for transmission through the user harnessing mechanism for forcibly and controllably interfacing the spinal mold mechanism and the neck aligning mechanism with the user's spine and neck, and, thereby guide posture modification and spinal alignment of the user according to the posture alignment goal.

The present disclosure provides a therapeutic device for eliminating or substantially reducing painful misalignments. This may result in significant improvements in personal appearance and maximize a user's energy with just a few minutes use per day. Using the disclosed apparatus as little as 12 minutes a day may restore the user's body's beautiful intended posture. This healthy posture may correct painful, destructive, misalignments and bring back the efficiencies that preserve the invaluable energy for productive and enjoyed daily activities.

A technical advantage of the disclosed subject matter includes improved the user's appearance. Posture is one of the most important elements of personal appearance. The method and system here disclosed provides entire body alignment, giving an attractive posture that is universally appealing to others.

A further technical advantage of the disclosed subject matter is increased energy. When posture is misaligned, a person burns incredible amounts of energy trying to compensate for the inefficiencies. Healthy humans are very efficient runners. The most efficient among us are able to run a marathon faster than a horse under the right conditions. When inactive and sedentary, an individual loses those efficiencies. The presently disclosed method and system help a user regain the user's structural efficiencies.

Yet a further advantage of the present method and system includes increased mobility. Posture is the largest factor determining of physical mobility. When posture is stiff and rigid, the person is stiff and rigid. People were designed to move and bend just as is any other living creature. The presently disclosed method and system provide the means to stretch, loosen, and balance physical range of motion to allow significantly improved freedom of motion.

Yet a further technical advantage is the avoidance of risky surgeries. Sometimes back surgery may necessary for back pain, but this should always be a last resort. The method and apparatus of the present disclosure may restore the user's back health without any surgeries.

Yet a further technical advantage of the present disclosure is the avoidance of dangerous prescriptions for back pain. We live in an overprescribed society. Prescription drugs may bring wonderful advancements in healthcare and treatment. But, they may also be abused and very dangerous. The subject matter of the present disclosure, in contrast, is completely drug free, but no less effective, for the right users.

Still another technical advantage of the presently disclosed subject matter is the elimination of downtime with initial product use. From the very first use, the present back therapy method and system start a rejuvenating process. While the user may experience an adjustment period, no restriction from daily activities occurs from the point of initial use. In fact, most users will notice an increased capacity right after the first use.

The novel subject matter of the present disclosure provides pneumatic posture alignment system that, when used consistently for just 15 to 25 minutes in the morning and again in the afternoon, provides the ability to correct a wide variety of posture problems, boost the user's energy level, and ease discomfort. As a therapeutic device, pneumatic posture alignment system has proven as effective to restore and preserve back health. For individuals needing back strength and resilience therapy, the presently disclosed pneumatic posture alignment system of the present disclosure provides a highly advantageous solution.

For a variety of kyphosis conditions, including, but not limited to, degenerative kyphosis, neuromuscular kyphosis, nutritional kyphosis, Scheuermann's kyphosis, traumatic kyphosis, and some forms of iatrogenic kyphosis (e.g., post-laminectomy kyphosis) the subject matter of the present disclosure has utility and may provide relief and cure as part of a physician's therapeutic or remedial regimen.

BRIEF DESCRIPTION OF THE DRAWINGS

The present subject matter will now be described in detail with reference to the drawings, which are provided as illustrative examples of the subject matter so as to enable those skilled in the art to practice the subject matter. Notably, the FIGUREs and examples are not meant to limit the scope of the present subject matter to a single embodiment, but other embodiments are possible by way of interchange of some or all of the described or illustrated elements and, further, wherein.

DETAILED DESCRIPTION OF ILLUSTRATIVE EMBODIMENTS

The detailed description set forth below in connection with the appended drawings is intended as a description of exemplary embodiments in which the presently disclosed process may be practiced. The term "exemplary" used throughout this description means "serving as an example, instance, or illustration," and should not necessarily be construed as preferred or advantageous over other embodiments. The detailed description includes specific details for providing a thorough understanding of the presently disclosed method and system. However, it will be apparent to those skilled in the art that the presently disclosed process may be practiced without these specific details. In some instances, well-known structures and devices are shown in block diagram form in order to avoid obscuring the concepts of the presently disclosed method and system.

In the present specification, an embodiment showing a singular component should not be considered limiting. Rather, the subject matter preferably encompasses other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present subject matter encompasses present and future known equivalents to the known components referred to herein by way of illustration.

The presently disclosed pneumatic posture alignment system provides a comprehensive system of three therapeutic devices designed to attain, and maintain, complete back health by correcting, and protecting, every aspect of the user's posture. In essence, the presently disclosed subject matter may be thought of as a "retainer" system for the body similar to a retainer used for teeth after braces.

The pneumatic posture alignment system of the present disclosure positions the curve of the spine with the position of the users shoulders and head. In viewing an individual from the side, there should be a straight line from the ear, to the shoulder, to the user's hips, and on down to the user's feet. This should be a straight line to assure her that there's proper spinal curvature of the individual. The users thoracic back should be right between the shoulder blades. The device of the present disclosure reshapes the user's body, the user's shoulders, head, hips, and feet alignment to a straight line, as opposed to a crooked line. When the user does this, a great deal of back pain is avoided or cured. So, discomfort and fatigue, and other adverse side effects due to a lack of alignment in an individual spine may be corrected. Alleviating these problems at an early stage also is highly effective in an early stage, preventing more serious problems later. This relief is a principal objective of the presently disclosed subject matter.

Figure 1:
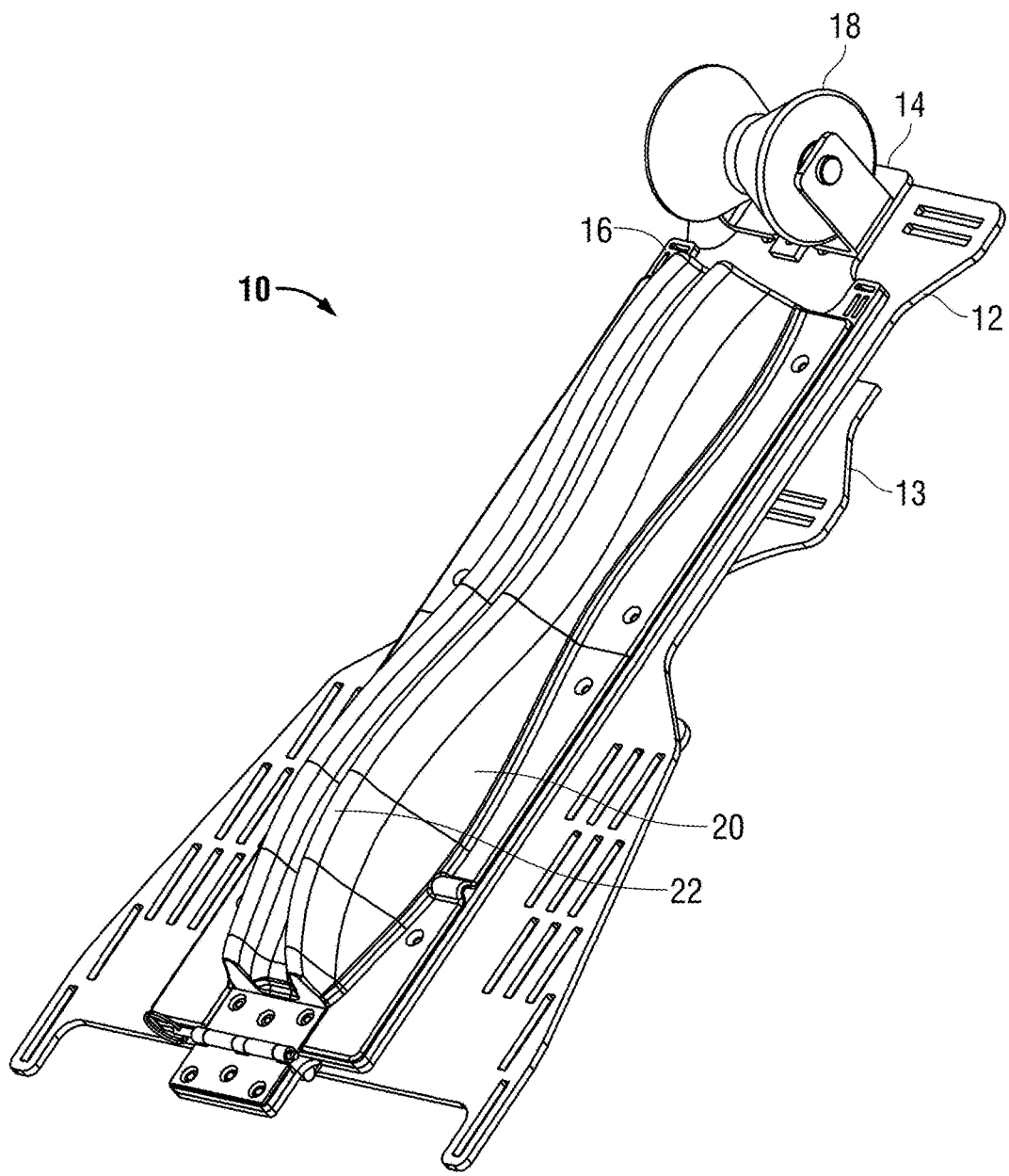
FIG. 1 shows an embodiment of pneumatic posture alignment system herein disclosed.

FIG. 1 shows an isometric view of pneumatic posture alignment system 10 of the present disclosure. Pneumatic posture alignment system 10 includes back plate 12 on which attaches separation plate 14. Separation plate 14 is positioned between back plate 12 and spinal mold plate 16. Attaching to separation plate 14 appears neck alignment mechanism 18. Spinal mold 20 attaches to spinal mold plate 16. Spinal guard rails 22 forms an integral part of spinal mold 20 and provides the posture modification and spinal alignment therapy of the presently disclosed posture alignment system 10.

Figure 2:
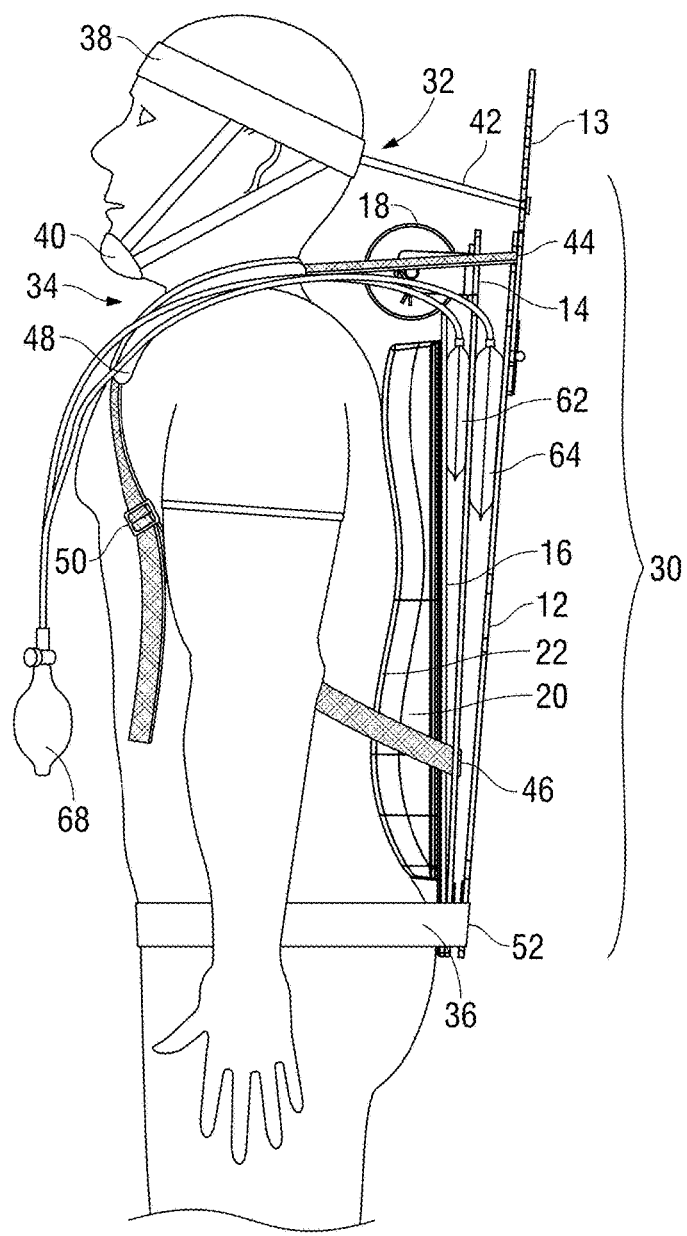
FIG. 2 shows an initial position of the posture alignment system posture alignment system on a user.

FIG. 2 illustrates use of posture alignment system 10 through the use user harness mechanism 30. User harness mechanism 30 includes three parts. These are head harness mechanism 32, shoulder harness mechanism 34, and hip harness mechanism 36. Head harness mechanism 32 includes headband 38. Attaching to headband 38 is chin harness 40. Chin harness 40 and headband 38 provide secure attachment structure for tether 42, which connects between back plate 12 and head harness mechanism 32, where tether 42 preferably attaches to headband 38.

Shoulder harness 34 attaches to separation plate 14 at the Attachment point 44 at the top of separation. 14 and to back plate 12 at attachment. 46 at the bottom of back plate 12. In addition, shoulder harness 34 includes shoulder pads 48, as well as adjustment buckle 50 to provide comfortable loading of posture alignment system 10 on the user's shoulders. In addition, hip harness 36 may attach to bottom portion 52 of separation plate 14.

In mounting the pneumatic posture alignment system 10, the user's grabs the unit by the back plate and lifts up the unit and flips around holding it with the left arm. Then, the user positions his arms through the shoulder straps and tightens the straps as though using a backpack. The device may then be held on the user's back using the shoulder straps. Also, pneumatic posture alignment system 10 uses a seatbelt around the user's waist. Thus, pneumatic posture alignment system 10 secures to the users back using both the shoulder straps and the seatbelt.

Once on the user's back, the user may adjust pneumatic posture alignment system 10 to a comfortable fit. Then, the back rail of the spinal mold 20 presses against the user's back and the user's neck will press against the neck alignment mechanism 18.

The headgear includes a chinstrap to secure the headgear firmly to the user's head. An elastic band is sewn into or otherwise firmly attaches to the headgear. By pulling the stretchy elastic band into position at the back plate notches, the base of the user's neck engages close and firmly with the neck alignment mechanism 18. The elastic band provides the desired tension between the headgear and the back plate. So, for this engagement, the user grabs the end of the tether cord and reaches back to grab the back plate. The user engages the stretchy cord into one of the notches in the back plate. Once the cord is secured within the back plate, the user may desire to adjust the device to a sure appropriate contact with the spine as well as general comfort level.

Figure 3:
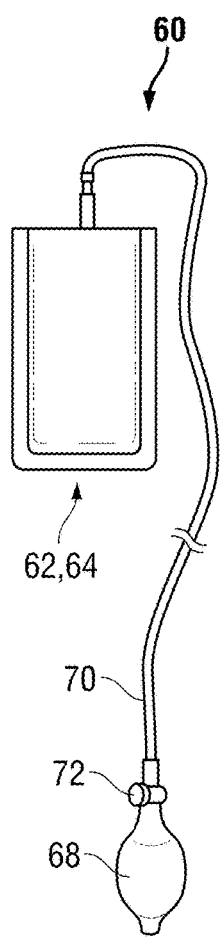
FIG. 3 illustrates an air shim device useful in one embodiment of the presently disclosed pneumatic posture alignment system.

FIG. 3 illustrates an air shim device useful in one embodiment of the presently disclosed pneumatic posture alignment system. In operation, one embodiment of posture alignment system 10 includes two air shims—a first air shim 54 positioned between separation plate 14 and spinal mold plate 16, and the second air shim 56 positioned between separation plate 14 and back plate 12.

Figure 4:
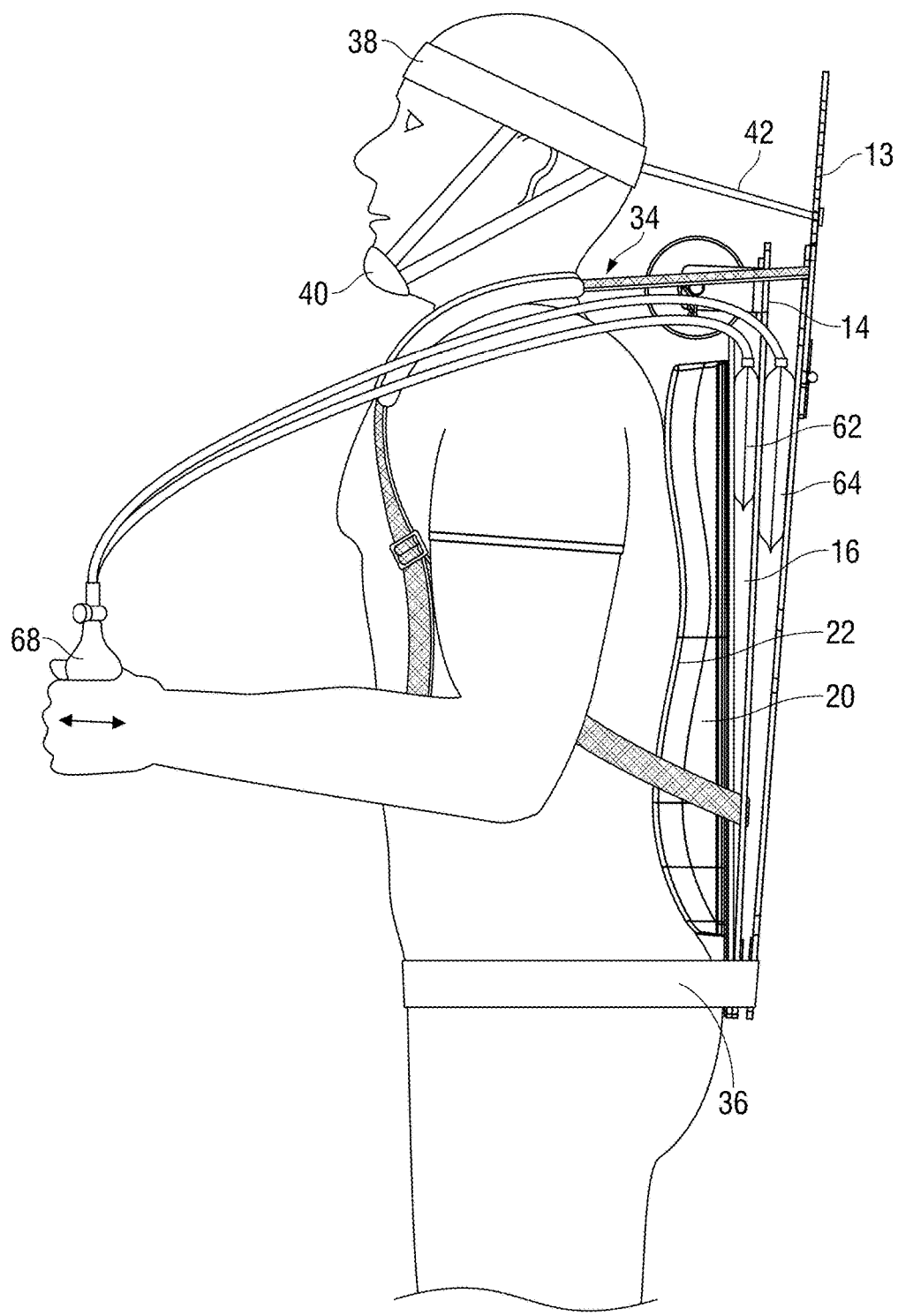
FIG. 4 an initial stage of use for the presently disclosed pneumatic posture alignment.
Figure 5:
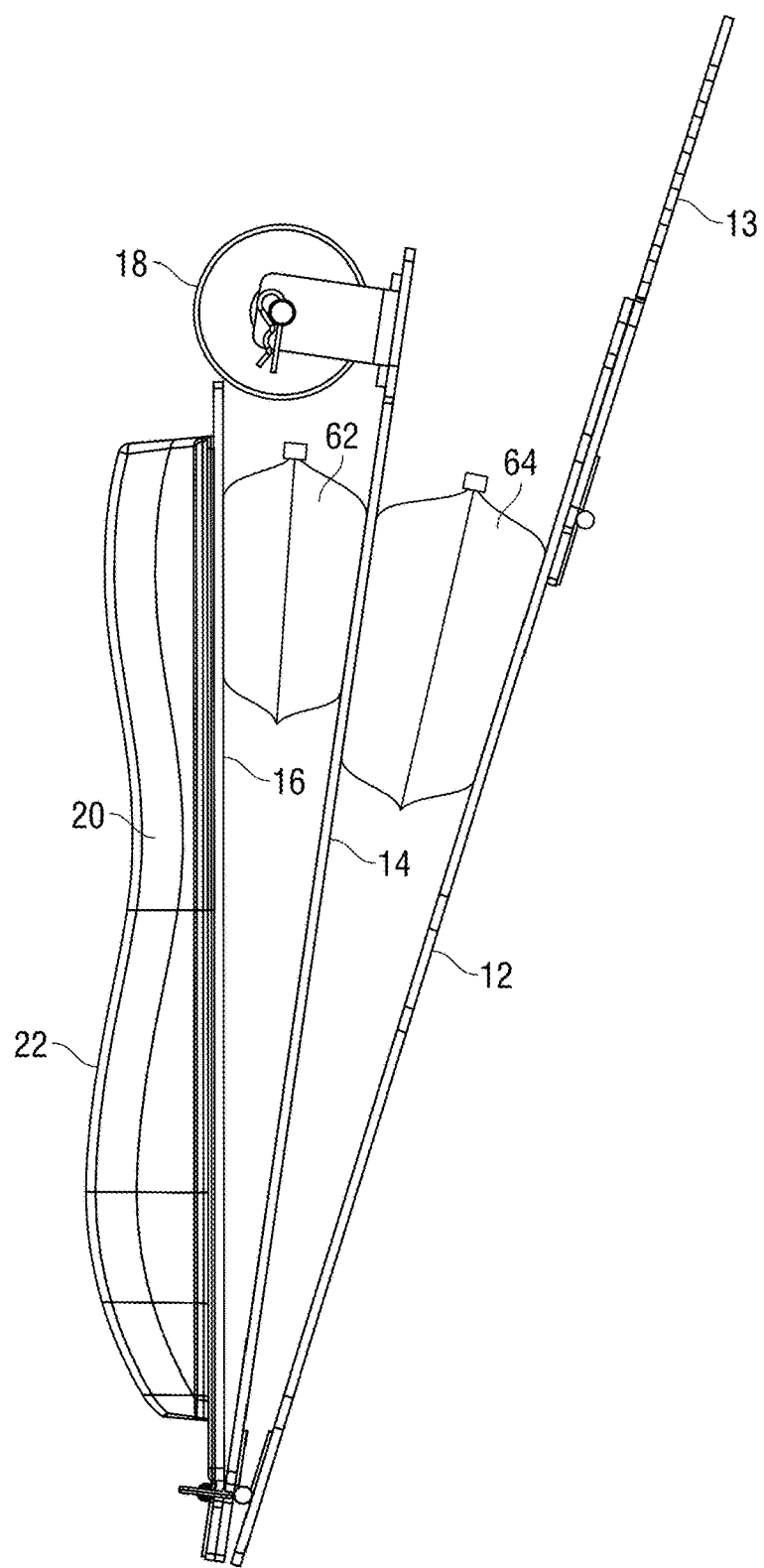
FIG. 5 illustrates a dual air shim system as may be useful in one embodiment of the presently disclosed system.
Figure 6:
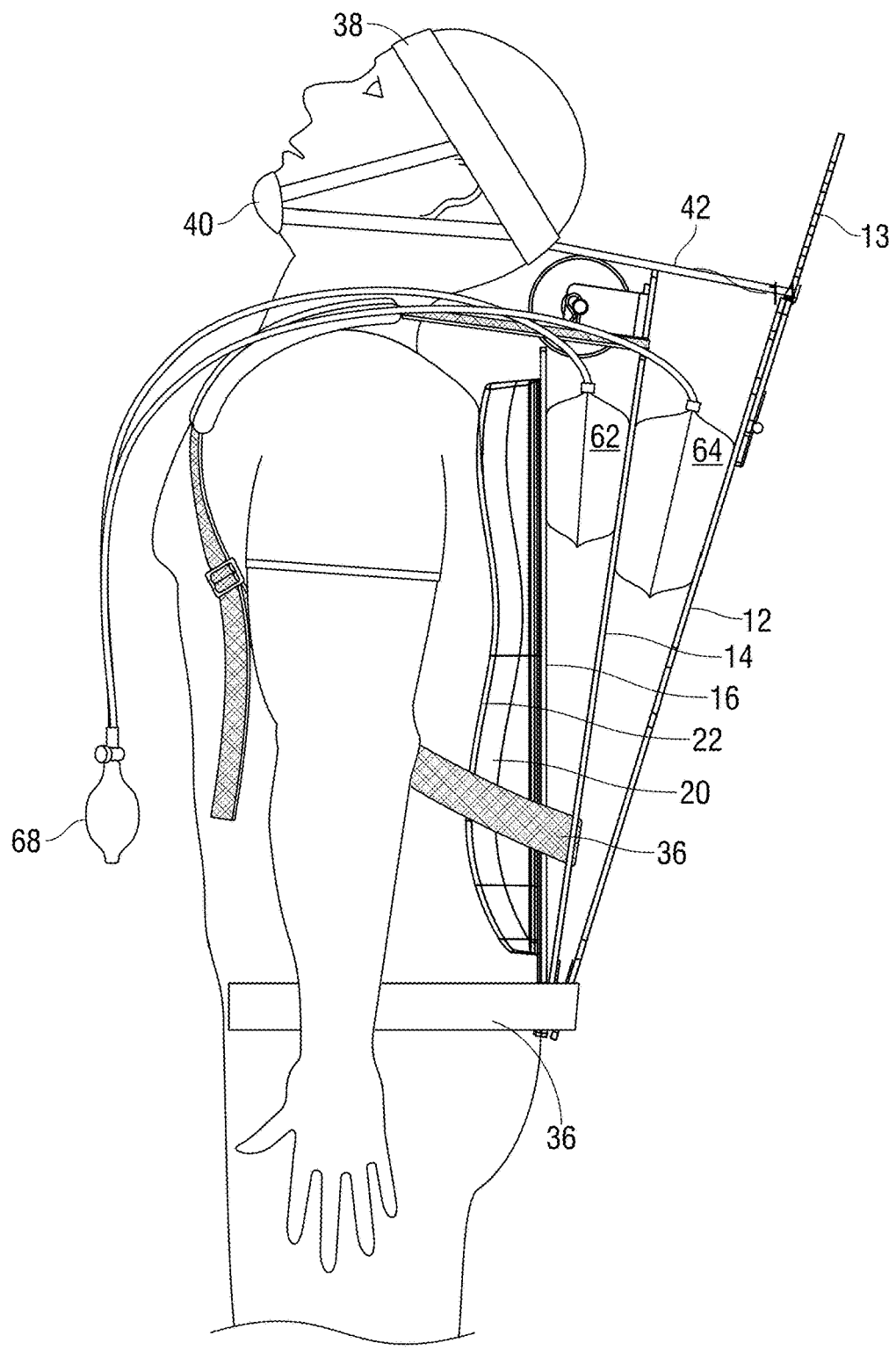
FIG. 6 shows a fully deployed configuration for the pneumatic posture alignment system.

FIGS. 4 through 6 illustrate implementation of the posture alignment system 10 of the present disclosure. Referring to FIG. 4, the user engages shim pump 58 to inflate air shims 54 and 56 from the initial deflated configuration a FIG. 4. Note that FIG. 5 the present disclosure shows that neck alignment mechanism 18 is secured to separation plate 14. Between spinal mold plate 16 and separation plate 14 appears air shim 54. Between separator plate 14 and back plate 12 appears air shim 56. With posture alignment system 10 positioned on the user's back, as described, air shim 54 and 56 may become fully inflated to provide a maximum amount of posture modification and spinal alignment for the presently disclosed configuration. This configuration places the greatest amount of stress on the user's back to provide the greatest amount of posture modification and spinal alignment therapy.

Figure 7:
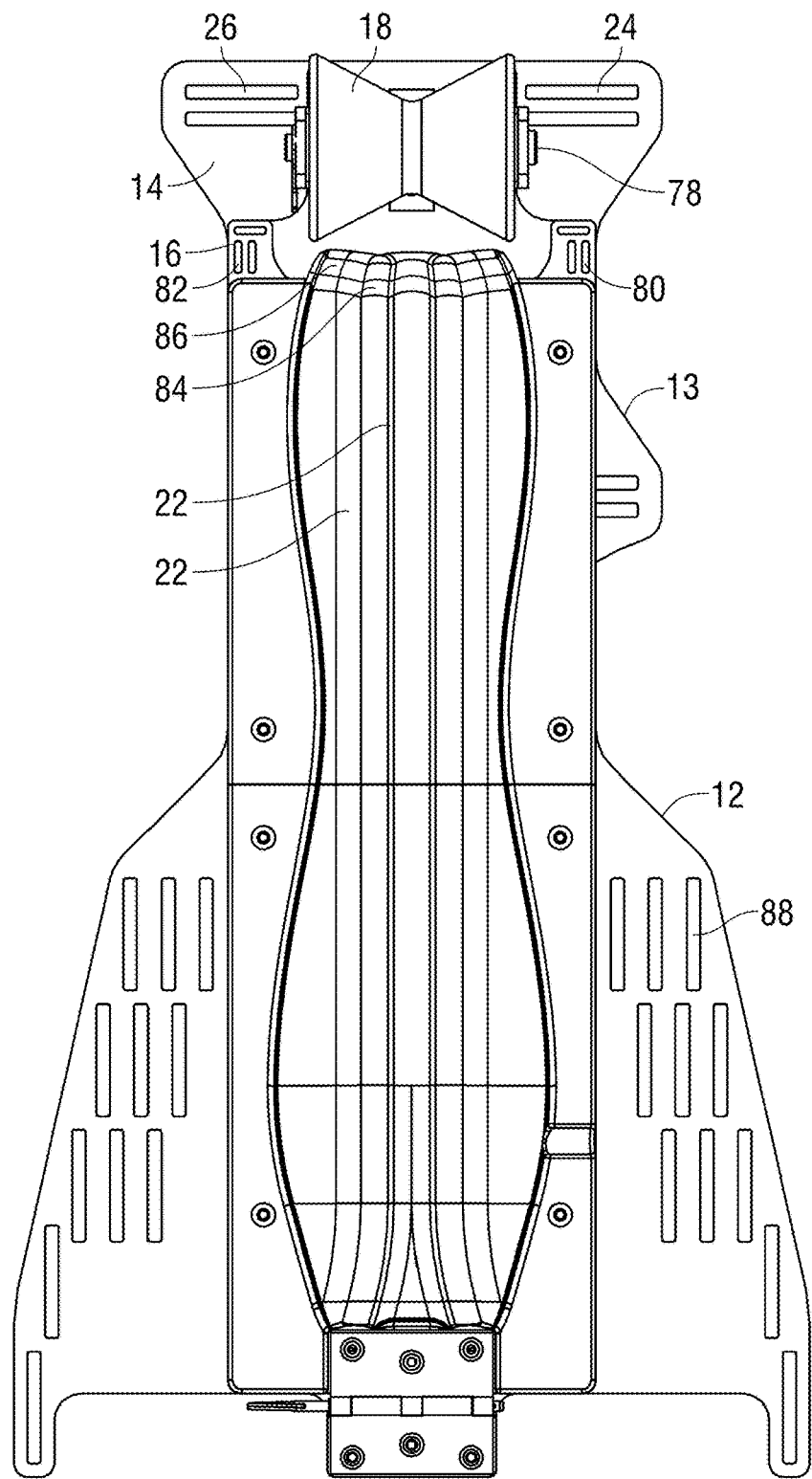
FIG. 7 highlights a front perspective of pneumatic posture alignment system.

FIG. 7 illustrates a front view of posture alignment system 10 wherein back plate 12 extends from the top of the configuration with strap openings 70 and 72 for attachment of shoulder harness mechanism 34. Neck alignment mechanism 18 takes an hourglass configuration and is connected to braces 74 for free rolling and movement within braces 74. The user's head engages posture alignment system 10 separation plate 14, in the configuration to FIG. 7 to extend above spinal mold plate 16 and can't receive straps for harnessing posture alignment system 10 on the user, via openings 76 and 78. Spinal mold 20, in the configuration to FIG. 7 extends along the links of spinal multiplied 16 and may even extend beyond spinal plate 16 through the use of extenders 80 and 82. These extenders allow spinal mold 20 to serve users of greater height than normal.

Also, on back plate 12 appear strap openings 84 and 86 that may accommodate straps for shoulder harness mechanism 34, as well as hip harness mechanism 36. One aspect of the device below the backpacks straps are slots. The slots are positioned in order to these provide slots for a restrictor strap that controls the inflation of the tension-producing bladder. Thus, in the event that the healthcare provider decides the amount of stress or the amount of adjustment that the device should perform, the slots in the positioning relative to the back plate lower limit. The limitation of the restrictor straps controls pneumatic posture alignment system 10 configuration so that the desired amount of movement occurs in aligning the user's posture.

The slots and restrictor strap control the positioning of the middle plate and back plate to provide the amount of adjustment that a particular user needs, according to an orthopedic or chiropractic therapy goal or improvement plan. Once the positions are determined and the restrictor strap is set, use of the device is limited positions and the amount of set change and will not exceed that limit. An important function of such a limit is to provide a position beyond which the user may hurt himself, but before which there is therapeutic benefit.

The function of the neck alignment mechanism 18 is to permit the ability to move the power roller up and down the device. This allows pneumatic posture alignment system 10 to accommodate individuals of different heights in different sizes in backs of different construction with different configuration of the pneumatic posture alignment system. Pneumatic posture alignment system 10 may be custom fit to the user's particular size shape and color and skeletal configuration. Neck alignment mechanism 18 may be adjusted up or down to fit the size of the particular user.

FIG. 7 highlights the configuration of the spinal mold 20 that the device for the present disclosure uses. In the present embodiment, the middle and back plates may be constructed of aluminum. In contrast, the spinal mold 20 may be formed of a rigid rubber or plastic material. The rubber or plastic that forms the spinal mold 20 flexible material, while at the same time having a certain degree of rigidity. The spinal mold 20 compresses only very slightly, e.g., a few millimeters, but generally has a rigid construction for the purpose of providing the support of interface for the back that the user needs. The flexible material provides a pleasant interface with the users back, but at the same time the rigid support that provides the therapeutic benefits of the disclosed pneumatic posture alignment system.

Figure 8:
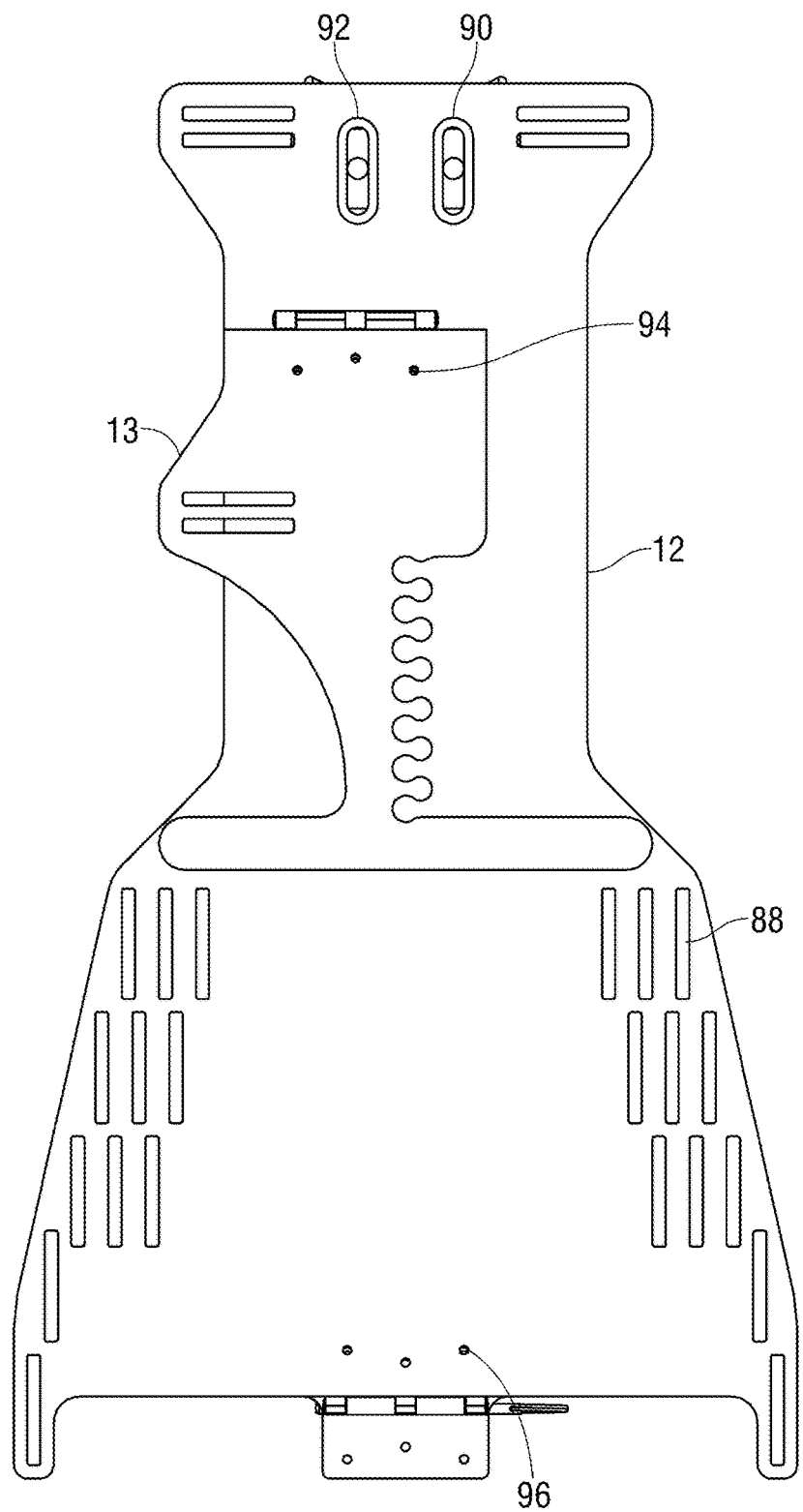
FIG. 8 shows a rear perspective view of the back plate for the presently disclosed pneumatic posture alignment system.

FIG. 8 shows the backside of back plate 12 including upper slots 70 and 72 for receiving the straps for shoulder harness mechanism 34. Also, appearing on the reverse side of back plate 12 are screw holes 90 and 92, which will be described below.

Pneumatic posture alignment system 10 includes three therapeutic devices: a full configuration, a retaining configuration, and a spinal mold configuration. These three device configurations of the disclosed pneumatic posture alignment system 10 work together to create a powerful synergy that restores and revitalizes the user's back in ways not possible until now.

The spinal mold configuration of FIG. 3C, with its carefully designed rails, will support and cradle the user's spinal column when using the full configuration and retaining configuration. The user's healthcare professional will custom fit the spinal mold configuration to the user's exact measurements. The rails are curved to restore the natural curves in the user's spinal column. The spinal mold configuration may be used independent of the full configuration and retaining configuration for a quick relaxing recharge anywhere and anytime the user needs it. The vibrating motor stays with the spinal mold configuration so the user may enjoy its rejuvenating massage on the go.

Next, a user may employ the retaining configuration to solidify the posture correction of the full configuration. The retaining configuration provides a compact version of the pneumatic posture alignment system. The retaining configuration uses a gentler kinetically enhanced engagement, without the head traction, so the user may use the retaining configuration in public and for longer periods of time. People around the user will see what appears to be a normal backpack, but the user will be using the presently disclosed neuro-physio reprogramming to completely reprogram the user's nervous posture alignment system to move the user's body with the healthy efficient posture the full configuration has helped restore.

The spinal mold 20 configuration of FIG. 3C, with its carefully designed rails, will support and cradle the user's spinal column when using the full configuration and retaining configuration. The user's healthcare professional will custom fit the spinal mold 20 configuration to the user's exact measurements. The rails are curved to restore the natural curves in the user's spinal column. The spinal mold 20 configuration may be used independent of the full configuration and retaining configuration for a quick relaxing recharge anywhere and anytime the user needs it. The vibrating motor stays with the spinal mold 20 configuration so the user may enjoy its rejuvenating massage on the go.

With all of its devices working together, pneumatic posture alignment system 10 provides a therapeutic posture alignment system fully capable of relieving and preventing excessive back discomfort, poor posture, and lack of energy. If the user's qualified healthcare professional approves, the user will receive the most technologically advanced, comprehensive, and effective back restoration, and revitalization possible. Pneumatic posture alignment system 10 of the present disclosure provides the user with the ability to achieve a healthy, attractive back supporting more actively engaging all normal activities and enjoyments of a healthy spine and back.

Figure 9:
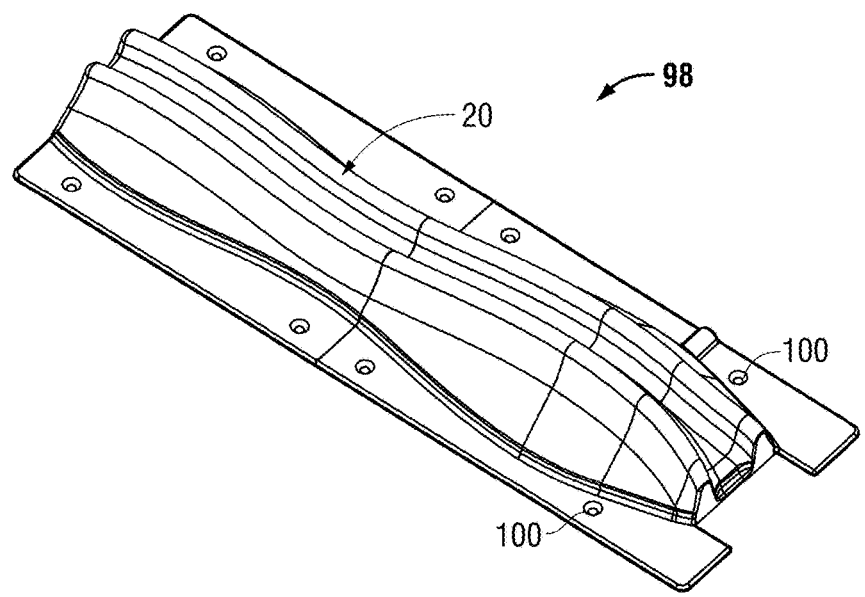
FIG. 9 shows a perspective view of the spinal mold configuration of the present pneumatic posture alignment system.
Figure 10:
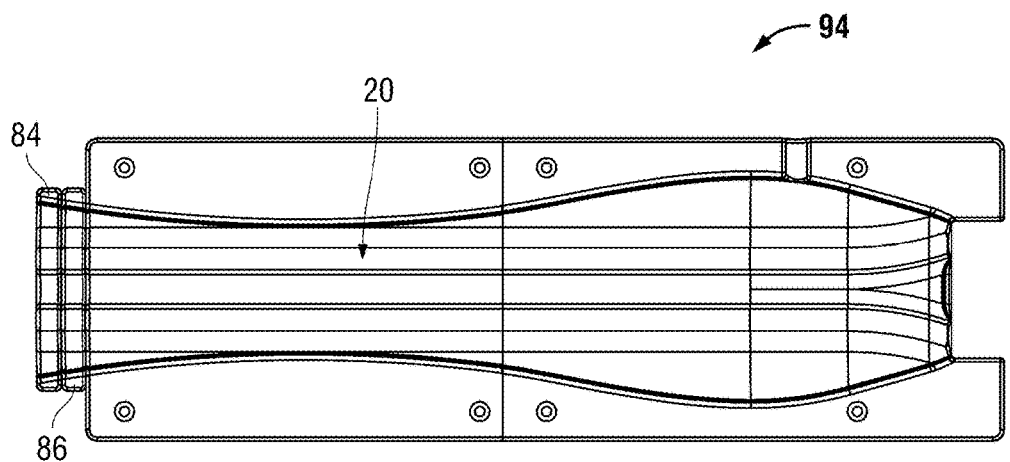
FIG. 10 presents a top-down view of the spinal mold structure of the presently disclosed pneumatic posture alignment system.

FIGS. 9 and 10 show in more detail the top side of spinal mold 20 appearing on spinal mold plate 16. This appears as a unit here referenced as spinal mechanism 94. Spinal mechanism 94 may be configured in multiple pieces or as a single unit according to manufacturing and assembly considerations. Screw holes 96 also provide for assembly of spinal mechanism 94 on separator plate 14 in this construction of posture alignment system 10. FIG. 10 provides a top-down perspective of spinal mechanism 94 to illustrate other dimensional characteristics of this portion of pneumatic posture alignment system 10.

Figure 11:
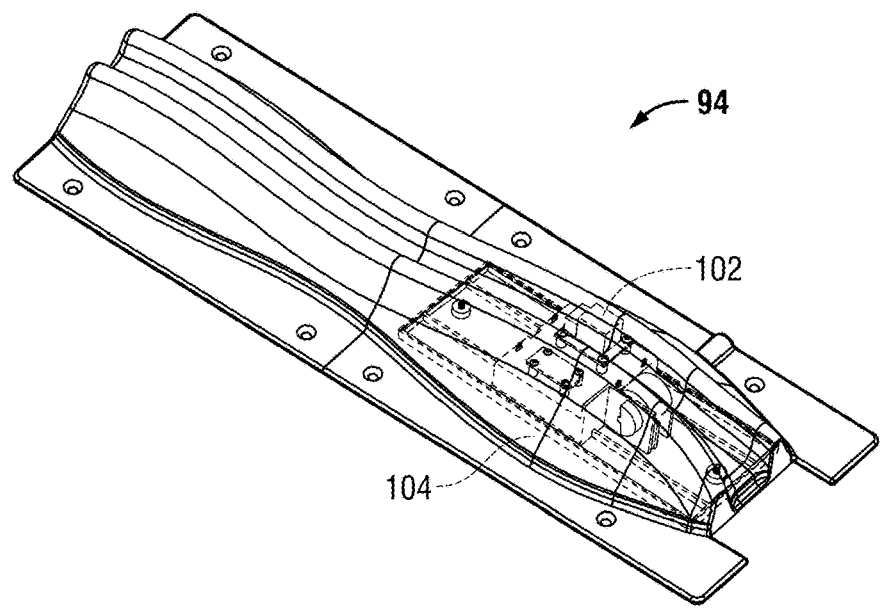
FIGS. 11 and 12 show aspects of the spinal mold configuration as a see-through image of the lumbar support region and the underlying vibrating motor.

FIG. 11 illustrates a cutaway perspective or transparent line perspective of posture alignment mechanism 94 to illustrate in more detail the position of vibration mechanisms 96. This appears also in an isometric view of the interior portion of the lower segment of posture alignment mechanism 94. Vibration mechanism 96 fits comfortably within lower portion 98 of spinal mechanism 94. Vibration mechanism 96 is a battery or other electric powered vibration mechanism that provides massaging vibration to the user as posture alignment system 10 is applied to the user's back.

Pneumatic posture alignment system 10 includes a vibration motor that may be actuated by a button on the base of the device, near the seatbelt. Upon actuation, pneumatic posture alignment system 10 vibrates and provides some massaging effect to the user's spine. With the massage motor operated, the user pumps the sports ball pump into the hose which connects to the bladder. The bladder inflates to separate the back plate from the middle plate. By virtue of inflating the bladder, the bladder increases in volume. This further causes the users shoulders to pull backwards during the inflation.

FIG. 11 shows an aspect of the spinal mold configuration as a see-through image of the lumbar support region and the underlying vibrating motor. The disclosure of the present body may include a battery-driven motor underneath the lumbar support region of the spinal mold 20. This provides the motor assembly that includes vibration cam motor that vibrates to a massage as the healing tension and alignment forces are applied to the users neck and back. The massaging effect from the vibrating motor facilitates circulation, as well as further promoting stretching or adjustment of the spinal posture alignment system. The motor may be very similar to that appearing in a massaging chair for promoting circulation agitation and adjustment as the stretching between the headpiece in the back of the head in the disclosed posture alignment system.

Another aspect of using an electrically powered vibration motor is the ability to use in controlling the duration of using presently disclosed pneumatic posture alignment system. A vibration motor with a timer set for 10 to 25 minutes provides a convenient control for posture alignment system use that is simply put to use by pushbutton operation for starting the vibration motor. By virtue of pushing the button, the user may initiate a 10-minute cycle, for example. The 10-minute cycle provides an ideal time for the stretching to occur as the bladder between the middle and back plates inflates, and the stretching between the user's head and neck occur for providing the tension for adjustment from the pneumatic posture alignment system. At the end of the 10-minute session, the user has received sufficient therapy for spinal alignment and the motor makes it clear that this time duration has occurred by turning off.

Figure 12:
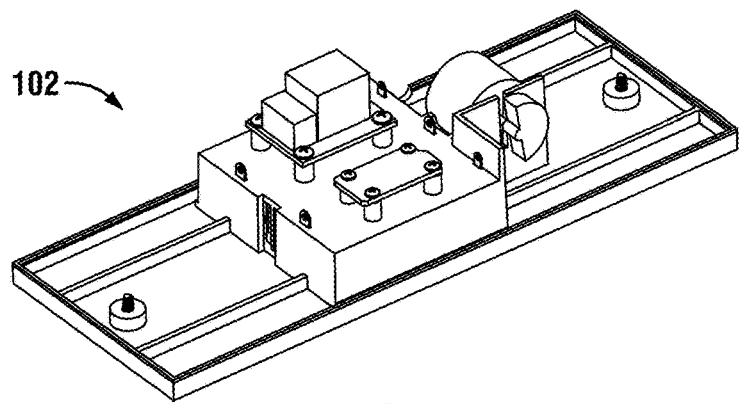
Figure 13:
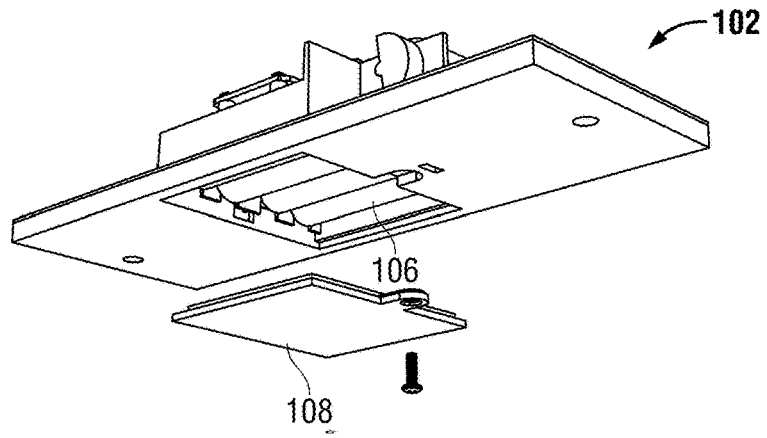
FIGS. 13 provides a bottom view of the spinal mold structure showing access to the battery compartment of the vibration motor within the spinal mold structure.

In addition, FIG. 13 shows how the vibration mechanism 96 fits within the molded structure of spinal mechanism 94 at lower portion 98 within spinal mechanism 94, FIGS. 12 and 13 further show the hinged arrangement for hinge 100 on which spinal mechanism 94 pivots. Hinges 102 and 104 show the arrangement for connecting separator plate 14 beneath spinal mechanism 94. With the arrangement of hinge 100 attached to spinal mechanism 94, and hinges 102 and 104 coupling separator plate 14. A wedged opening area can be formed between back plate 12 and separator plate 14 as the upper area of separator plate 14 swings out and about on hinges 102 and 104. Likewise, as spinal mechanism 94 pivots on hinge 100, an opening or separation taking away the shape between the upper portion of separator plate 14 and spinal mechanism 14. It is within these wedged openings that air shims 54 and 56, respectively, can take increasing volume is to provide the posture modifying and spine aligning forces of the present disclosure.

The hinges that are designed for quick release and quick attachment of the spinal mold 20. A heavy-duty door hinge fastens the middle plate to the back plate. The pneumatic posture alignment system, therefore, includes three plates. The top plate that includes the spinal mold 20 for forming the alignment of the spine. The other two plates are the metal plate and the back plate.

Of importance is the fact that the bladder operation and the motor operation are independent of one another. Thus, the user may not desire to use the vibration that the motor provides, but may only desire a constant pressure that the bladder provides for aligning the spinal posture alignment system. In contrast, user may seek the massaging effect that the motor provides, but not want to have the additional aligning tension that the bladder expansion provides. In either instance, in using the posture alignment system the present disclosure of the user has discretion of providing one aspect or another or both that the bladder in the motor provide.

Figure 14:
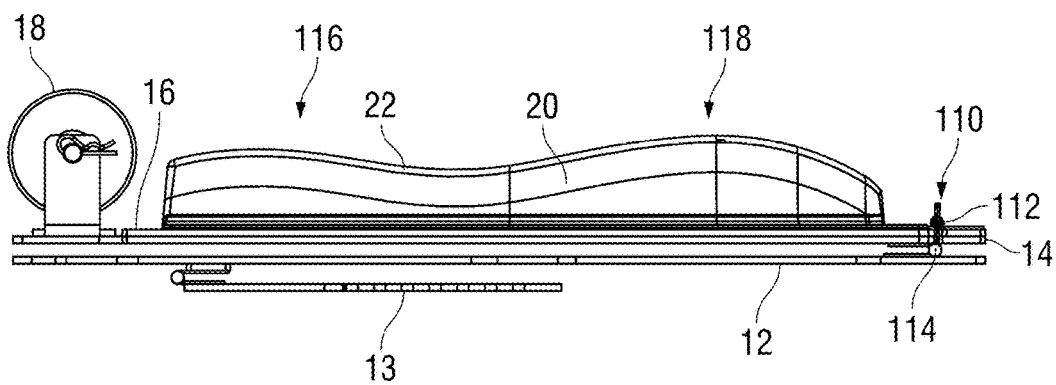
FIG. 14 shows side view of a back-spinal mold configuration that is applicable to therapy for a user's upper and lower back regions.

FIG. 14 illustrates a side perspective view of a spinal mechanism 94 that provides posture modification and spinal alignment for both the upper portion of the users back by virtue of the raised segment 106 and the lower portion of the users back through what raised section 108. FIG. 14 also shows a side view of neck alignment mechanism 18 to illustrate the respective associations of neck alignment mechanism 18 with spinal mechanism 94. Of interest in FIG. 14 is the side perspective view of spinal mold 20 plate 16 supporting part of spinal mechanism 94 with hinge 100. The side view of hinge 104 shows how a parallel separation exists between back plate 12 and separator plate 14.

Figure 15:
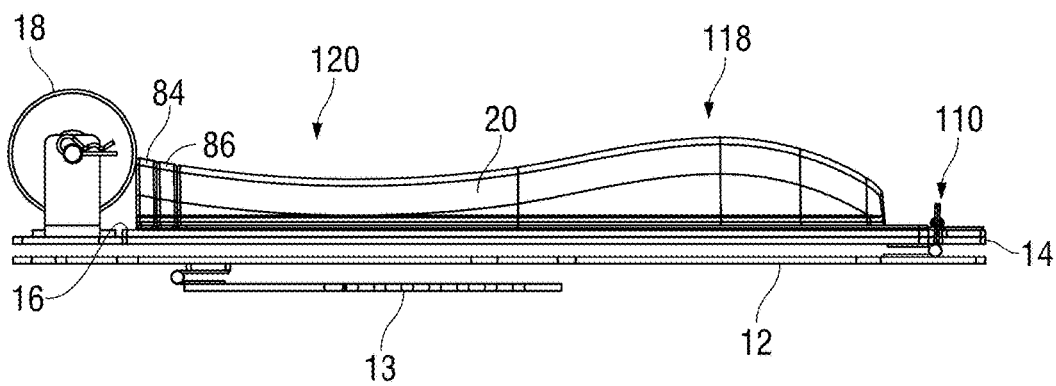
FIG. 15 shows a side view of a back-spinal mold configuration that is applicable to therapy for a user's lower back region only.
Figure 16:
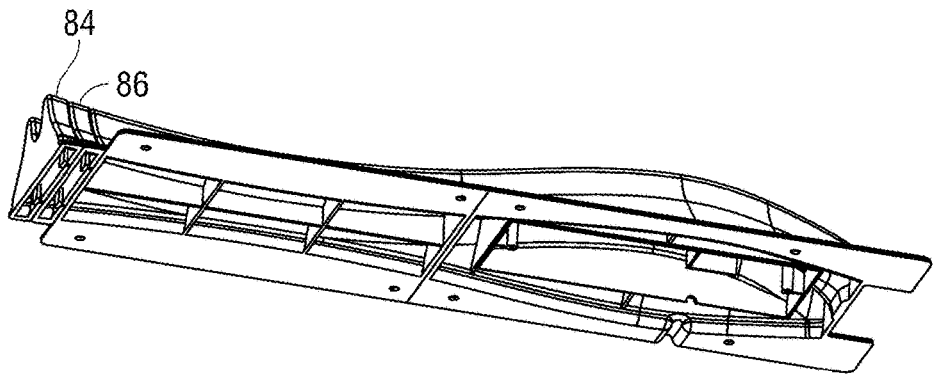
FIG. 16 shows the extenders at the top between the spinal mold plate and the roller device for accommodating taller users.

FIGS. 15 and 16 show another configuration of posture alignment system 10 wherein spinal mechanism 94 takes an alternative configuration of supplying lower back posture modification and alignment. FIG. 15 is designed for a curved back, but providing a more gentle stretch in the back. Because of the more gentle stretch of this natural curve configuration, the user usually may wear posture alignment system 10 for a longer period of time. Although spinal mechanism 94 provides guide rails at the upper portion 110, there is not as much posture modification as might be occurring at lower portion 112. In addition, referring to both FIGS. 15 and 16, there appear extensions 80 and 82 for the purpose of allowing spinal mechanism 94 to serve taller users.

Figure 17:
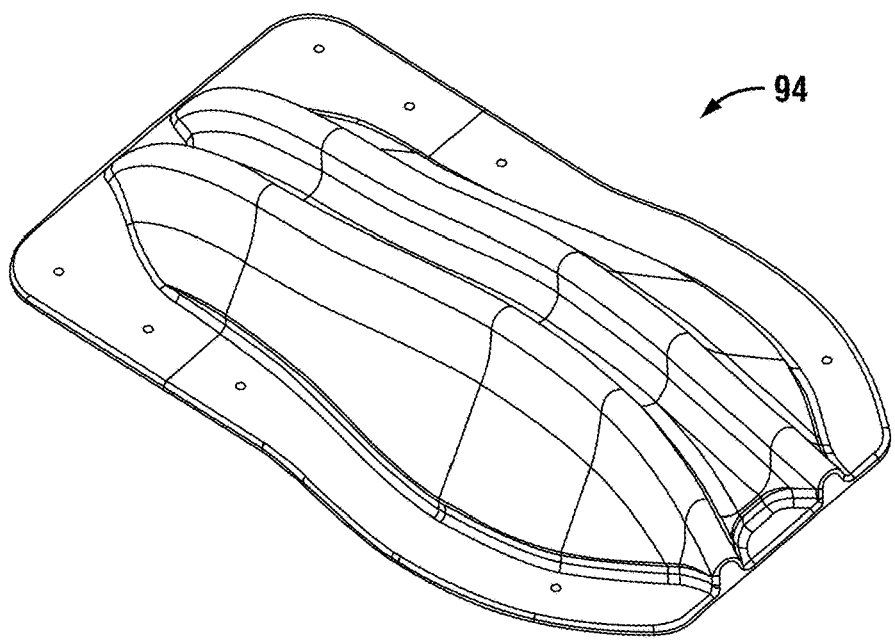
FIGS. 17 and 18 illustrate isometric view of spinal mold configurations for lower and upper-lower back treatments, respectively.
Figure 18:
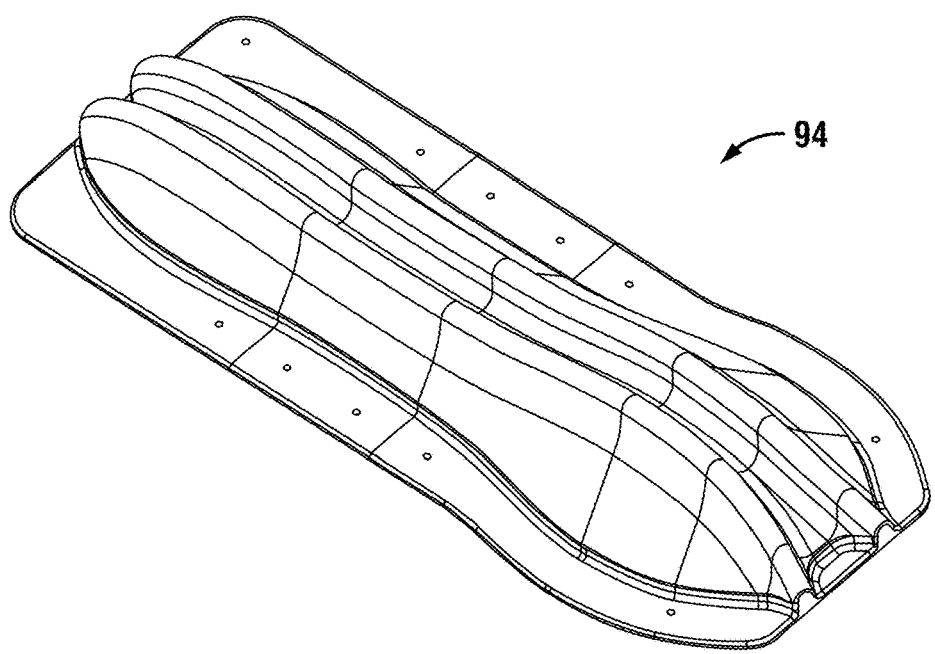

FIGS. 17 and 18 illustrate isometric views of spinal mechanism 94 showing lower posture modification and spinal alignment. In contrast, spinal mechanism 94 of FIG. 18 provides both upper and lower pasture modification and support and corresponds to the side view construction of FIG. 14.

The spinal mold configuration uses the body's own weight to apply controlled pressure to the spinal vertebrae. As the user presses his spine firmly against the length of the two contoured rails of the spinal mold configuration to fit the natural shape of the mid and lower back, the vertebrae in the spine are gradually and gently encouraged to realign into their natural positions. This realignment helps to relieve back pain and improve overall mobility.

The spinal mold configuration helps relieve muscular pain, pressure and irritation and provides the best home therapy for relieving back tension and stress. In use, the spinal mold configuration cradles and elevates the spine, isolating the vertebrae into a neutral position where gravity takes over and allows the vertebrae to naturally and properly realign. This process helps relieve symptoms common to misalignment problems, since the basic concept has to do with biomechanics and proper alignment.

In the spinal mold configuration, the curvature of the mold is dictated by the proper alignment of the back. The design considers benefits to the user's lumbar support at the bottom of the mount. The thoracic region is at the top of the spinal mold configuration, i.e., the smaller mount of the spinal mold 20. The use of the spinal mold configuration sets the curve on the use of his lumbar and then apply the curve to the thoracic.

A particular advantage of the presently disclosed spinal mold configuration is the ability to vary the size of the configuration according to the size and needs of user. By virtue of the neck alignment mechanism 18, upon which the user places the neck, any person of normal size may use the posture alignment system. The adjustable height and lateral position of the neck alignment mechanism 18 allows adjustment in the effective size of the spinal mold configuration. This allows the user to adjust the spinal mold configuration to a most comfortable setting.

The spinal mold configuration is without the neck alignment mechanism 18 configuration for the neck, as well as without the bladder and back plate. The retaining configuration of FIG. 18 is sufficiently small and with a sufficiently sleek profile to be placed under a coat or sweater for other piece of clothing if desired. The retaining configuration simply looks like a backpack. At the same time, the retaining configuration provides the configuration adjustment and the therapeutic effect of the present posture alignment system. Accordingly, looking like a backpack it provides no reason for the user to stand out in the crowd as the user walked out in public.

The retaining configuration of FIG. 18 does not pull the user's head back and neck back to provide aligning the therapeutic tension, but it does reinforce and retain the benefits of the full configuration. The retaining configuration pulls the shoulders back and places the spinal mold 20 against the user's spine. Accordingly, the retaining configuration provides a highly beneficial retaining function for the user who is also using the entire on the device.

Figure 19:
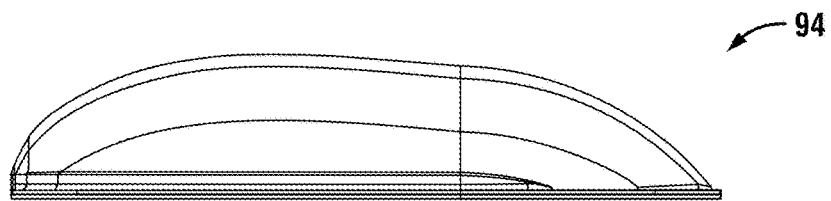
FIGS. 19, 20, and 21 show side perspective view of various configurations of spinal mold configurations for varying user therapies.
Figure 20:
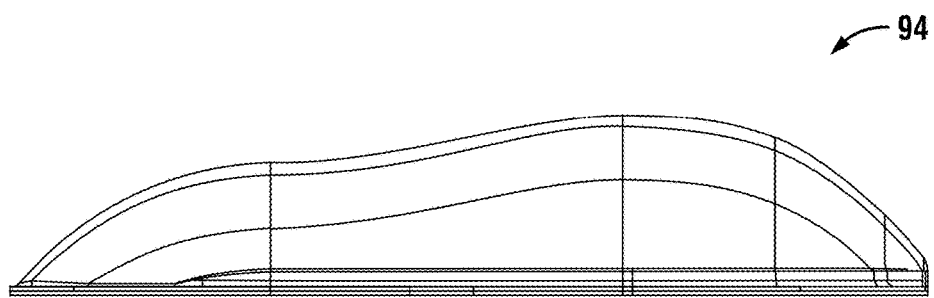
Figure 21:
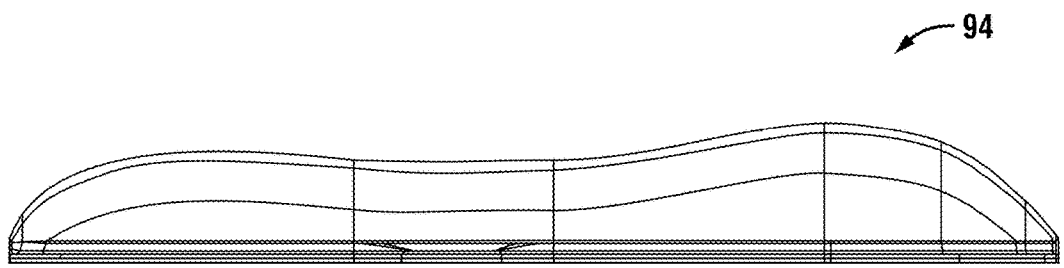

FIGS. 19 through 21 illustrate further variations of the present disclosure. It FIG. 19, only the upper configuration of spinal mold appears. At FIG. 20, a configuration for addressing therapy to only the lower portion of the users back.

The configuration of FIG. 20 relates to the situation where the user may have problems only in the lumbar region. The configuration of FIG. 20 facilitates the alignment of the lumbar disc of the user by loosening up and stretching the user's lumbar region when the user lays on the device. This would not, however, provide treatment for the thoracic region, as would be the FIG. 19 configuration. So, the FIG. 20 configuration pertains to the instance where a user specifically has problems with the lumbar region, such as when a user must first address lumbar region problems prior to using the posture alignment system for addressing the entire back. FIG. 21 shows the configuration for using the spinal mold configuration to treat an entire back.

Pneumatic posture alignment system 10 employs ergonomic product development, and creates new technology that may quickly restore and revitalize the user's back in ways not possible until now. The presently disclosed pneumatic posture alignment system 10 incorporates three new, groundbreaking, technologies that advances back healthcare with specific benefits to the user. these benefits include (a) omnidirectional dynamic restructuring; (b) kinetically enhanced engagement; and (c) neuro-physio reprogramming, as here described.

Omnidirectional Dynamic Restructuring: Pneumatic posture alignment system 10 literally pushes and pulls the user's head, spinal column, shoulders, and hips in every possible direction needed to correct the very structure of his body. This will give the user the elusive straight line connecting his head, shoulders, hips, and feet to achieve greatly improved posture. This straight line very strongly promotes total back health and helps the user appear physically attractive to others.

Kinetically Enhanced Engagement: Pneumatic posture alignment system 10 may be used while standing up and walking around. This engagement allows infinite micro-adjustments to occur in the user's posture that could only occur while he is upright and mobile. The presently disclosed pneumatic posture alignment system 10 may quickly restore posture, because of its engaging every muscle, joint, and tissue in the body that is involved with posture. Complete back health even requires coordination from the feet, so use of pneumatic posture alignment system 10 occurs with standing and walking during each session.

Neuro-Physio Reprogramming: Lasting posture improvement occurs when a user's nervous system holds structural corrections in place through reprogramming muscle memory. Neural reprogramming, for better or worse, normally occurs gradually over time. With the presently disclosed pneumatic posture alignment system, reprogramming occurs quickly. Because of the intensity, duration, and totality of engagement, neuro-physio reprogramming occurs rapidly and deeply within the individual's muscle and nerve memories. Soon the user's resting posture will be correct posture. The successful user of the presently disclosed pneumatic posture alignment system 10 experiences no more straining to "stand up straight."

The presently disclosed system and method of operation are different from other therapeutic devices by being based on spinal manipulation. In addition, the present system and method also involve the head, shoulders, hips, and feet in ways that were yet to be imagined before now. Because of this complete engagement, pneumatic posture alignment system 10 may correct most common back problems more effectively and efficiently than ever thought possible and keep the user's back healthy the user's entire life.

Using pneumatic posture alignment system 10 applies pressure similar to having a spinal manipulation. A chiropractor is doing this when he performs an adjustment. The main difference is that a pneumatic posture alignment system 10 treatment is over ten-minute segments which conditions the body to change its very structure. If a patient may receive a spinal manipulation treatment, it is likely that a healthcare professional will approve the user for the presently disclosed pneumatic posture alignment system.

Pneumatic posture alignment system 10 here disclosed is intended for individuals of general good health who only have common back problems or who wish to prevent such problems. These individuals will have passed a full evaluation by a qualified healthcare professional and have been trained in spinal manipulative therapy, to verify the pneumatic posture alignment systemic right for them.

Pneumatic posture alignment system 10 provides a highly attractive option for a person with common back problems. This is true, because pneumatic posture alignment system 10 provides the most technologically advanced, comprehensive, and effective back restoration and revitalization possible. No other therapeutic device may restore, revitalize, and protect a user's back as quickly, safely, and effectively as the presently shown pneumatic posture alignment system 10.

Another aspect of the disclosed pneumatic posture alignment system 10 includes benefits for those who may yet not have common back problems. An individual may not presently have back problems, but his lifestyle may be leading towards back problems in the future. Using pneumatic posture alignment system 10 of the present disclosure will serve to prevent back problems that may prove difficult to reverse later. For individuals susceptible to such condition, the disclosed subject provides a solution for easily preventing back problems that may be much more difficult to treat later.

Even in the situation where only the appearance of an individual's back may be of concern. Pneumatic posture alignment system 10 here disclosed may reverse poor posture and give the use a beautiful straight line connecting the head, shoulders, hips, and feet. Such straightly aligned posture is known to be both attractive and conducive to use being perceived as both youthful and strong. The straight line that the presently disclosed method and system provide, are not only visually attractive, but will keep the user's back healthy as pneumatic posture alignment system 10 balances the load on each curve in the back.

The presently disclosed pneumatic posture alignment system 10 may be used for a daily 15-minute session in the morning and a 15- to 30-minute session in the afternoon. The user's healthcare professional may work with the user to establish and monitor a specific regimen and use frequency.

A further aspect of the presently disclosed subject matter derives from there being no bulky or constricting braces or other apparatus to wear under the user's clothing. An individual may use pneumatic posture alignment system 10 at home, work, or anywhere the user may stand or walk for 15 to 30 minutes. Even when the user may have no time to spare, pneumatic posture alignment system 10 may be of great value.

Yet a further benefit of the presently disclosed method and system is its ability to provide with user with more energy throughout the day. The pain and energy losses that the presently disclosed pneumatic posture alignment system 10 addresses rob individuals of precious energy through the day. By helping the user to attain optimal back health, the presently disclosed subject matter may dramatically raise his energy to further help him become more effective and efficient with the user's time.

Pneumatic posture alignment system 10 here disclosed may provide very aggressive posture correction. Depending on the regimen a healthcare professional may approves, there may be some temporary soreness and discomfort as a direct result of using the pneumatic posture alignment system. Even with less aggressive treatment, there may still be some soreness, as the user's body adjusts to the treatment. Clearly, his current general condition strongly influences how his body responds to the pneumatic posture alignment system. As with any medication or medical device use, the individual should immediately stop using pneumatic posture alignment system 10 and consult his healthcare professional if experiencing anything beyond the level of soreness and discomfort expected by the prescribed treatment level.

The posture alignment system of the present disclosure complements and does not replace the advice and medical counsel of a qualified healthcare professional trained in spinal manipulative therapy. These individuals may include a (a) chiropractor, (b) osteopathic physician, (c) naturopath physician, (d) physical therapist, and/or (e) orthopedic physician. The combination of the method and system of the present disclosure and the medical treatment of a qualified healthcare professional provides the very best path to back health and repair for essentially any condition.

The posture alignment system has three treatment levels which represent increasing amounts of engagement. Within each level, the user may opt to stretch his body or to hold its proper shape. Level 1 is a quick, gentle, and relaxing stretch of the back that may be a warm up the next levels or a stand-alone option. Level 2 adds a stretch of the shoulders and allows a user to walk around inside or outside. Level 2 is also where the body is being trained to hold correct posture while upright. Level 3 adds the head and neck for a complete body realignment.

The three levels of treatment may range from very mild and gentle to very intense and aggressive. The user may control the intensity based on his ability to handle the pressures created. Treatment times range from 12 minutes in Levels 1 and 3 and 30 minutes or more in Level 2.

The posture alignment system is based on spinal manipulation for aligning the head, shoulders, hips, and feet. The complete engagement of the posture alignment system may correct most common back and joint problems more effectively and efficiently than ever thought possible and keep the user's posture healthy the user's entire life.

There are many products that engage the spine and shoulders, but none are capable of the complete engagement a user enjoys with the posture alignment system. Most of them simply may not generate the force needed to effectively reverse misalignments. The posture alignment system may generate all the force needed to correct even the most stubborn posture issues for the brawniest person.

The posture alignment system applies pressure similar to having a spinal manipulation. A chiropractor is doing this when they perform an adjustment. The main difference is that a posture alignment system treatment is over timed 10 minute increments which conditions the body to change its very structure. Being able to receive a spinal manipulation treatment is an indication that a user may use the posture alignment system.

A user will feel results immediately. There is an immediate therapeutic benefit from the very first use. Any relief from back tension will always be felt instantly much like a relaxing massage. He will be amazed at the level of tension a user have simply gotten used to.

Results a user may see will depend on many factors. Here is a list of a few of those factors. The user's age affects results, because younger users will typically see results faster. The user's fitness level age affects results, because the fitter a user is, the more responsive the user's body will be to positive changes. The severity of the user's misalignments age affects results, because the more exaggerated the user's spinal curvature, the more force and time it will take to see significant change. And, the user's overall flexibility age affects results, because, in general, posture issues are a result of a loss of flexibility which causes a loss in range of motion. The more rigid and muscular a user are, the more effort it will take to see changes.

Provided that a misalignment is the user's only issue, a user will see results. Some people will see them faster than others. The posture alignment system is intended for individuals of general good health who have, or wish to prevent, common back and joint problems, or those who want to maximize their energy and efficiency levels. These individuals will have passed a full evaluation by a qualified healthcare professional, trained in spinal manipulative therapy, to verify there are no underlying issues that need medical attention.

Some users will only want the spinal mold 20 for a gentle, revitalizing stretch that will slowly adjust the user's posture and bring therapeutic relief from stress and tension. Others will want to aggressively address poor posture and be willing to endure some discomfort to get there with the highest level of treatment.

The posture alignment system may have a significant impact on the user's athletic performance. Optimum athletic performance requires proper body alignment. The posture alignment system may ensure his body's structure is tuned to perfection so the user's maximum athletic potential is realized. The user's body needs to be aligned just as much as a car needs to be in proper alignment to perform at its full potential and avoid unnecessary damage.

The posture alignment system may also help if the only issue is the appearance of the user's posture. The posture alignment system may reverse poor posture and give him the beautiful straight line connecting his head, shoulders, hips, and feet that others find visually attractive. This straight line is not only visually attractive, but also will keep the user's back and joints healthy as it balances the user's weight on every load bearing point in the user's body. Losing this straight line is one of the main reasons back and joint problems occur.

The posture alignment system is based around sessions that may be as short in duration as 12 minutes or up to 30 minutes or more. The sessions may be in the morning, afternoon and/or evening. The user may get a simple, rejuvenating, massage and slight tune up in about 12 minutes using only the spinal mold 20. The user may go up to 1 hour on a long walk outside as well. His healthcare professional may help him set up a specific frequency. There are no bulky or constricting braces or other apparatus to wear under the user's clothing during the day. a user may use the posture alignment system at home, work, or anywhere a user may lay, stand or walk.

The posture alignment system is capable of very aggressive posture correction if using the posture alignment system to its fullest potential. If the user's healthcare professional approves the more aggressive approach, there will be some temporary soreness and discomfort as a direct result while using the posture alignment system. Even with the mildest treatment there may still be some soreness as his body adjusts to its unique dynamic. The posture alignment system incorporates four technologies which are the cornerstones of its effectiveness. These four technologies include the following:

Omnidirectional dynamic restructuring: The posture alignment system may literally push and pull the user's head, spinal column, shoulders, and hips in every possible direction needed to correct the very structure of the user's body. This will give him the beautiful straight line connecting his head, shoulders, hips, and feet that all people with great posture have. This straight line is paramount to total back health and looking the user's best.

Kinetically enhanced engagement: Another feature of the posture alignment system is that a user may apply it while standing up walking around. This engagement allows infinite micro-adjustments to occur in his posture that could only occur while he is upright and mobile. The posture alignment system quickly restores the user's posture, because it engages every muscle, joint, and tissue in his body that is involved with posture. Complete back health even requires coordination from the user's feet so he stands or walks during advanced sessions.

Neuro-physio reprogramming: Lasting posture improvement only occurs when the user's body's muscle memory is reprogrammed to hold structural corrections in place. Neural reprogramming, for better or worse, normally occurs gradually over time. With the posture alignment system, this reprogramming occurs quickly because of the intensity, duration, and totality of engagement. Soon his resting posture will be correct posture.

Mobility range correction: The posture alignment system may safely stretch the user's back to increase his range of motion to correct the imbalance. This new balance makes it effortless for a user to stand straight without having to strain. The posture alignment system operates at three optional treatment Levels, each with two types of engagement, to accommodate the different goals and needs of each user. These three Levels may work together to create a powerful synergy that restores and revitalizes the user's back in ways not possible until now. Here is a brief summary of each Level:

As the most basic level, Level 1 requires only one of the two the small, portable, spinal molds. One mold will stretch, and decompress, the user's spine to increase his range of motion. The other mold will train the user's spine to rest with the healthy curvature nature intended. The user simply places the spinal mold 20 on the floor, lays on it, and starts the vibrating motor, it's that simple. The vibrating motor inside the spinal mold 20 will add a rejuvenating massage to the experience and stop after 10 minutes so he may just relax. With its carefully designed rails, the spinal mold 20 will support and cradle the user's spinal column during each session. The spinal mold 20 will be custom fit to the user's exact measurements once a user is medically cleared.

After Level 1, Level 2 may further correct the user's posture by allowing him to be upright. Being upright helps him realign his shoulders, hips, and feet. First, the user secures the spinal mold 20 of his choice, via the quick and easy release hinges, to the aluminum plates. Using the straps on the plates, the user puts the posture alignment system on just like an ordinary backpack. The user then tightens the straps positioned to his waist and shoulders. The user inflates the air shim between the middle and back plate and feels the straps pulling his shoulders back relative to his spine pressing the mold into his back. The user then activates the vibrating motor and moves about freely. Level 2 uses kinetically enhanced engagement, neuro-physio reprogramming, and mobility range correction to train the user's body to move efficiently while upright and mobile. People around a user will see what appears to be a normal backpack, but the user will be restructuring his back, shoulders, hips, and feet to move together with all of the efficiencies intended by nature.

Also after Level 1, a user may wish to go even further to correct the posture. Again, the user puts on the posture alignment system just like an ordinary backpack, but stays indoors as Level 3 would be unsafe for outside use. The user then secures the shoulder and waist straps, along with the head traction, and inflate the appropriate air shims to their appropriate level. The user starts the soothing vibrating motor and, in just 10 minutes, the posture alignment system will engage all four of its powerful technologies to realign the user's head, back, shoulders, hips, and feet in the beautiful straight line nature intended. Level 3 is the most intense level, as it applies powerful, but balanced, pressure to counter all of the alignment hazards our bodies are subjected to.

With all of the three levels working together, the posture alignment system makes possible complete body alignment. If the user's qualified healthcare professional approves, a user will receive the most technologically advanced, comprehensive, and effective posture restoration and revitalization possible, period.

According to various novel aspects of the present disclosure, here appears a posture alignment system and methods of use for improving the posture of a user by posture modification and spinal alignment. The novel and inventive subject matter includes a back plate for positioning the posture alignment system along a user's back and in alignment with the spine when the user is standing. The back plate provides a rigid structural foundation extending from approximately the user's head down vertically to at least to the user's hip region. A separation plate hingedly couples to the posture alignment system at a position near the user's hip region when positioning the posture alignment system along the user's back. The separation plate has a length approximately the length of the back plate may be positioned in parallel with the back plate for forming a first variable wedge space from the back plate upon being pivoted at the hinged coupling.

A spinal mold mechanism has a length approximately equivalent to that of and positioned in parallel with the separation plate. The spinal mold mechanism hingedly couples to the posture alignment system near (i.e., adjacent or essentially in contact with,) the user's hip region when positioning the posture alignment system along the user's back. The spinal mold mechanism includes a spinal mold 20 positioned on the spinal mold plate and has a length equal to at least approximately the length of the user's spine for interfacing and providing posture modifying support and alignment force to the user's spine. The spinal mold mechanism includes posture alignment guide rails for guiding posture modification and spinal alignment according to a posture alignment goal. A spinal mold plate provides structural support and foundation for the spinal mold 20 and forms a second variable wedged space from the separation plate upon being pivoted at the hinged coupling.

A neck aligning mechanism on the posture alignment system is above the spinal mold 20 when positioning the posture alignment system along the user's back for aligning the position of the user's neck with the user's spine. In this configuration, the posture alignment guide rails guide the posture modification and spinal alignment.

A user harnessing mechanism harnesses the posture alignment system to the user. The user harnessing system includes a head harnessing mechanism further including at least one head harness for firmly harnessing the user's head and a tether harness for firmly connecting set head harness to the back plate. A shoulder harness mechanism including at least one harness for each shoulder of the user for firmly harnessing the user's shoulders to the spinal mold mechanism. A hip harness for harnessing the user's hips to the posture alignment system.

A pneumatic force generating mechanism associates with the back plate, the separation plate, and the spinal mold mechanism for controllably generating pneumatic force at the spinal mold back plate for transmission through the user harnessing mechanism for forcibly and controllably interfacing the spinal mold mechanism and the neck aligning mechanism with the user's spine and neck, and, thereby guide posture modification and spinal alignment of the user according to the posture alignment goal.

The detailed description set forth herein in connection with the appended drawings is intended as a description of exemplary embodiments in which the presently disclosed subject matter may be practiced. The term "exemplary" used throughout this description means "serving as an example, instance, or illustration," and should not necessarily be construed as preferred or advantageous over other embodiments.

This detailed description of illustrative embodiments includes specific details for providing a thorough understanding of the presently disclosed subject matter. However, it will be apparent to those skilled in the art that the presently disclosed subject matter may be practiced without these specific details. In some instances, well-known structures and devices are shown in block diagram form in order to avoid obscuring the concepts of the presently disclosed method and system.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein, but is to be accorded the widest scope consistent with the principles and novel features disclosed herein. It is contemplated that additional embodiments are within the spirit and true scope of the disclosed subject matter.

I claim:

1. A posture alignment system for improving the posture of a user by posture modification and spinal alignment according to a predetermined posture alignment goal, comprising:

a back plate for positioning said posture alignment system along a user's back and in alignment with the spine when the user is standing, said back plate providing a rigid structural foundation configured to extend from approximately the user's head down vertically to at least to the user's hip region;

a separation plate hingedly coupled to said posture alignment system at a position configured to be adjacent the user's hip region when positioning said posture alignment system along the user's back, said separation plate having a length approximately the length of said back plate and positionable in parallel with said back plate and further for forming a first variable wedge space from said back plate upon being pivoted at a hinged coupling;

a spinal mold mechanism having a length approximately equivalent to that of and positioned in parallel with said separation plate, said spinal mold mechanism being hingedly coupled to said posture alignment system adjacent the user's hip region when positioning said posture alignment system along the user's back, said spinal mold mechanism further comprising:

a spinal mold positioned on said spinal mold plate mechanism and having a length equal to at least approximately the length of the user's spine for interfacing and providing posture modifying support and alignment force to the user's spine, said spinal mold comprising a posture alignment guide rails for guiding posture modification and spinal alignment according to a posture alignment goal; and a spinal mold plate for providing structural support and foundation for said spinal mold and for forming a second variable wedged space from said separation plate upon being pivoted at said hinged coupling; and a neck aligning mechanism on said posture alignment system and positioned to be above said spinal mold when positioning said posture alignment system along the user's back for aligning the position of the user's neck with the user's spine, as said posture alignment guide rails guide said posture modification and spinal alignment;

a user harnessing mechanism for harnessing said posture alignment system to the user, further comprising a head harnessing mechanism further comprising at least one head harness for firmly harnessing the user's head and a tether harness for firmly connecting set head harness to said back plate;

a shoulder harness mechanism comprising at least one harness for each shoulder of the user for firmly harnessing the user's shoulders to said spinal mold mechanism; and a hip harness for harnessing the user's hips to said posture alignment system; and a pneumatic force generating mechanism for associating said back plate, said separation plate, and said spinal mold mechanism for controllably generating pneumatic force at said spinal mold plate for transmission through said user harnessing mechanism for forcibly and controllably interfacing said spinal mold mechanism and said neck aligning mechanism with the user's spine and neck, and, thereby guide posture modification and spinal alignment of the user according to said posture alignment goal.

2. The posture alignment system of claim 1, further comprising a vibration mechanism for vibrating and applying massaging vibration to the user's spine when the user wears said posture alignment system for enhancing said posture modification and spinal alignment force.

3. The posture alignment system of claim 1, wherein said pneumatic force generating mechanism further comprises an air shim for controllably spacing said separation plate from said back plate for controllably varying the force applied during said forcibly and controllably interfacing said spinal mold mechanism and said neck aligning mechanism with the user's spine and neck.

4. The posture alignment system of claim 1, wherein said pneumatic force generating mechanism further comprises a first pneumatic air shim positioned in said first variable wedge space for controllably spacing said separation plate from said back plate and a second pneumatic air shim positioned in said second variable wedge space for controllably spacing said separation plate from said spinal mold plate for controllably varying the force applied during said forcibly and controllably interfacing said spinal mold mechanism and said neck aligning mechanism with the user's spine and neck.

5. The posture alignment system of claim 1, wherein said neck aligning mechanism further comprises an hourglass-shaped roller mechanism for permitting smooth controlled positioning of the user's neck when interfacing said neck aligning mechanism.

6. The posture alignment system of claim 1, wherein said head harnessing mechanism further comprises a headband for harnessing said harnessing mechanism to the user's head and a chin harness for harnessing said head harnessing mechanism to the user's chin for firmly harnessing said posture alignment system to the user.

7. The posture alignment system of claim 1, wherein said spinal mold further comprises a lower back mold for modifying and aligning the posture of the user's lower back region.

8. The posture alignment system of claim 1, wherein said spinal mold further comprises an upper and lower back mold for modifying and aligning the posture of the user's upper and lower back regions.

9. A method for improving the posture of a user by posture modification and spinal alignment according to a predetermined posture alignment goal, comprising the steps of:

positioning a posture alignment system along a user's back and in alignment with the spine when the user is standing using a back plate, said back plate providing a rigid structural foundation extending from approximately the user's head down vertically to at least to the user's hip region;

forming a variable separation between said back plate and a separation plate, said separation plate hingedly coupled to said posture alignment system at a position adjacent the user's hip region when positioning said posture alignment system along the user's back, said separation plate having a length approximately the length of said back plate and positionable in parallel with said back plate and further for forming a first variable wedge space from said back plate upon being pivoted at a hinged coupling;

forming a separation between said separation plate and a spinal mold mechanism having a length approximately equivalent to that of and positioned in parallel with said separation plate, said spinal mold mechanism being hingedly coupled to said posture alignment system adjacent the user's hip region when positioning said posture alignment system along the user's back, said spinal mold mechanism further comprising:

interfacing and providing posture modifying support and alignment force to the user's spine using a spinal mold positioned on said spinal mold plate and having a length equal to at least approximately the length of the user's spine, said spinal mold comprising a posture alignment guide rails for guiding posture modification and spinal alignment according to a posture alignment goal; and providing structural support and foundation for said spinal mold and forming a second variable wedged space from said separation plate upon being pivoted at said hinged coupling using a spinal mold plate; and aligning the position of the user's neck with the user's spine, as said posture alignment guide rails guide said posture modification and spinal alignment using a neck aligning mechanism on said posture alignment system, said neck aligning mechanism positioned to be above said spinal mold when positioning said posture alignment system along the user's back;

harnessing said posture alignment system to the user using a user harnessing mechanism, said harnessing further comprising the steps of:

firmly harnessing the user's head using a head harnessing mechanism comprising at least one head harness for and a tether harness for firmly connecting set head harness to said back plate;

firmly harnessing the user's shoulders to said spinal mold mechanism using a shoulder harness mechanism comprising at least one harness for each shoulder of the user; and harnessing the user's hips to said posture alignment system using a hip harness; and associating said back plate, said separation plate, and said spinal mold mechanism for controllably generating pneumatic force at said spinal mold back plate for transmission through said user harnessing mechanism using a pneumatic force generating mechanism for forcibly and controllably interfacing said spinal mold mechanism and said neck aligning mechanism with the user's spine and neck, and, thereby guiding posture modification and spinal alignment of the user according to said posture alignment goal.

10. The posture aligning method of claim 9, further comprising the steps of vibrating and applying massaging vibration to the user's spine when the user wears said posture alignment system for enhancing said posture modification and spinal alignment force using a vibration mechanism.

11. The posture aligning method of claim 9, further comprising the steps of controllably spacing said separation plate from said back plate for controllably varying the force applied during said forcibly and controllably interfacing said spinal mold mechanism and said neck aligning mechanism with the user's spine and neck using an air shim.

12. The posture aligning method of claim 9, further comprising the steps of controllably spacing said separation plate from said back plate using a first pneumatic air shim positioned in said first variable wedge space and controllably spacing said separation plate from said spinal mold plate using a second pneumatic air shim positioned in said second variable wedge space, said first and second pneumatic air shim controllably varying the force applied during said forcibly and controllably interfacing said spinal mold mechanism and said neck aligning mechanism with the user's spine and neck.

13. The posture aligning method of claim 9, further comprising the steps of permitting smooth controlled positioning of the user's neck when interfacing said neck aligning mechanism using an hourglass-shaped roller mechanism.

14. The posture aligning method of claim 9, further comprising the steps of harnessing said harnessing mechanism to the user's head using a headband and harnessing said head harnessing mechanism to the user's chin using a chin harness for firmly harnessing said posture alignment system to the user.

15. The posture aligning method of claim 9, further comprising the steps of modifying and aligning the posture of the user's lower back region using a lower back spinal mold as said spinal mold.

16. The posture aligning method of claim 9, further comprising the steps of modifying and aligning the posture of the user's upper and lower back regions using upper and lower back spinal mold as said spinal mold.

17. A detachable spinal mold mechanism for detachable use with a posture alignment system for improving the posture of a user by posture modification and spinal alignment according to a predetermined posture alignment goal, comprising:

a spinal mold mechanism having a length approximately equivalent to that of and positioned in parallel with a back plate of the posture alignment system, said spinal mold mechanism being hingedly coupled to said posture alignment system and configured to be adjacent the user's hip region when positioning said posture alignment system along the user's back, said spinal mold mechanism further comprising:

a spinal mold positioned on said spinal mold plate and having a length equal to at least approximately the length of the user's spine for interfacing and providing posture modifying support and alignment force to the user's spine, said spinal mold comprising a posture alignment guide rails for guiding posture modification and spinal alignment according to a posture alignment goal; and a spinal mold plate for providing structural support and foundation for said spinal mold and for forming a second variable wedged space from said separation plate upon being pivoted at a hinged coupling; and a neck aligning mechanism on said posture alignment system and positioned to be above said spinal mold when positioning said posture alignment system along the user's back for aligning the position of the user's neck with the user's spine, as said posture alignment guide rails guide said posture modification and spinal alignment;

a user harnessing mechanism for harnessing said posture alignment system to the user, further comprising a shoulder harness mechanism comprising at least one harness for each shoulder of the user for firmly harnessing the user's shoulders to said spinal mold mechanism; and a hip harness for harnessing the user's hips to said posture alignment system;

said spinal mold mechanism being detachably associated with a back plate for positioning said posture alignment system along a user's back and in alignment with the spine when the user is standing, said back plate providing a rigid structural foundation extending from approximately the user's head down vertically to at least to the user's hip region;

a separation plate hingedly coupled to said posture alignment system at a position adjacent the user's hip region when positioning said posture alignment system along the user's back, said separation plate having a length approximately the length of said back plate and positionable in parallel with said back plate and further for forming a first variable wedge space from said back plate upon being pivoted at said hinged coupling; and a pneumatic force generating mechanism for associating said back plate, said separation plate, and said spinal mold mechanism for controllably generating pneumatic force at said spinal mold back plate for transmission through said user harnessing mechanism for forcibly and controllably interfacing said spinal mold mechanism and said neck aligning mechanism with the user's spine and neck, and, thereby guide posture modification and spinal alignment of the user according to said posture alignment goal.

18. The detachable spinal mold mechanism of claim 17, wherein said spinal mold further comprises a lower back mold for modifying and aligning the posture of the user's lower back region.

19. The detachable spinal mold mechanism of claim 17, wherein said spinal mold further comprises an upper and lower back mold for modifying and aligning the posture of the user's upper and lower back regions.

* * * * *